United States Patent [19]

Chazot et al.

[11] Patent Number: 4,854,355
[45] Date of Patent: Aug. 8, 1989

[54] STEPWISE ADVANCING ROTARY CONVEYOR AND INSTALLATION FOR TAKING LIQUID SAMPLES INCORPORATING SUCH A CONVEYOR

[75] Inventors: Henri Chazot, Les Angles; Gérard Cauquil, Bagnols Sur Ceze; Jean-Paul Muller, Orsan, all of France

[73] Assignee: Cogema-Compagnie Generale Des Matieres Nucleaires, France

[21] Appl. No.: 175,779

[22] Filed: Mar. 31, 1988

[30] Foreign Application Priority Data

Apr. 9, 1987 [FR] France ............................. 87 04998

[51] Int. Cl.⁴ ............................................. G01N 1/14
[52] U.S. Cl. ..................................... 141/130; 141/98; 141/168; 141/329; 198/341; 198/345; 422/100; 366/219; 414/626; 73/863.01; 73/863.81; 73/863.91
[58] Field of Search ............... 414/626; 198/341, 345, 198/859; 141/130, 1, 98, 329, 330, 168, 69, 11; 422/100; 366/219, 237; 73/863.01, 863.91, 863.92, 863.81, 864.81

[56] References Cited

U.S. PATENT DOCUMENTS

| | | | |
|---|---|---|---|
| 3,405,455 | 10/1968 | Strong | 34/20 |
| 3,512,624 | 5/1970 | Crane | 198/341 |
| 3,686,960 | 8/1972 | Tarbet | 74/1.5 |
| 3,921,821 | 11/1975 | Champion et al. | 73/863.91 |
| 3,981,546 | 9/1976 | Sperman | 384/12 |
| 4,276,260 | 6/1981 | Drbal et al. | 422/100 |
| 4,354,796 | 10/1982 | Bergman | 414/676 |
| 4,422,151 | 12/1983 | Gilson | 141/130 |
| 4,581,583 | 4/1986 | Van Vliet et al. | 73/863.01 |
| 4,708,940 | 11/1987 | Yoshida et al. | 422/100 |
| 4,761,268 | 8/1988 | Andersen et al. | 422/100 |

FOREIGN PATENT DOCUMENTS 101192  2/1984  European Pat. Off.

*Primary Examiner*—Ernest G. Cusick

[57] ABSTRACT

For passing stepwise bottles (F, F') in front of different stations, in order to more particularly take liquid samples, the bottles are placed in receptacles formed on a plate (24). The rotation of the plate is ensured by a lifting support action using compressed air delivered by injectors (18). Immediate rotation stoppage is obtained when a hole (38) formed in plate (24) faces the end of an optical fiber, whereof the opposite end issues onto an optical detector. Associated with an automatic sampling and dilution system, the assembly can be advantageously installed in a glove box or shielded enclosure in the nuclear industry.

10 Claims, 3 Drawing Sheets

STEPWISE ADVANCING ROTARY CONVEYOR AND INSTALLATION FOR TAKING LIQUID SAMPLES INCORPORATING SUCH A CONVEYOR

BACKGROUND OF THE INVENTION

The invention relates to a rotary conveyor making it possible to move containers, such as bottles in stepwise manner past a certain number of fixed stations. The invention also relates to the application of such a conveyor to the construction of an automated installation for taking liquid samples from bottles sealed by caps with a view to analyzing these samples.

The performance of certain chemical processes makes it necessary to periodically take samples of products at different stages of the process, in order to analyze them to check their characteristics.

In the nuclear industry, these sampling operations are complicated by the fact that they have to be carried out within glove boxes or shielded enclosures ensuring the protection of the personnel located outside the same.

When the sampling operations involve occasional checks performed in the laboratory, use is presently made of glass pipettes having a spherical ground joint connected to a syringe in their upper part. Each sampling operation is carried out by immersing the pipette tip into the liquid to be sampled and then drawing up the liquid with the syringe. The sampled quantity is checked by means of a micrometric screw fitted to the syringe.

It is obvious that the operation of such equipment requires numerous handling operations remotely performed by the operator, e.g. with the aid of a remote manipulator or invaginated gloves in the wall of the cell. Thus, to the handling operations necessary for performing the sampling operation are added the need to rinse the glassware and wipe the outside of the pipette after each sampling operation. Therefore this equipment is difficult to use when relatively closely spaced periodic sampling operations have to be carried out on an industrial installation.

In addition, the glassware must be frequently replaced and the equipment must incorporate devices making it possible to unplug and replug the bottles.

Finally, the volumes supplied are imprecise, because they are in particular dependent on the delivery speed of the liquid, the viscosity of the solution, the cleanness of the glassware and the adjustment of the meniscus to the calibration mark of the pipette.

Furthermore, the presently available conveyors for automatically passing samples in front of various stations cannot be used within a glove box or a shielded enclosure, as required by the nuclear industry.

Thus, the installations used in confinement cells must be subdivided into a mechanical part located within the cell and a control part located outside, which is not possible with existing conveyors.

Moreover, all existing conveyors have mechanisms which cannot be used in a radioactive medium without undergoing significant modifications. This also applies to the materials forming these mechanisms and which are usually incompatible with a radioactive environment.

Finally, the existing automatic conveyors have excessive dimensions to permit their integration into the cell in which the available volume is limited. Moreover, their cost is very high, if account is taken of the fact that an installation in a confinement cell containing radioactive products has to be periodically replaced.

SUMMARY OF THE INVENTION

The invention specifically relates to a stepwise advancing rotary conveyor, whose design and construction are particularly well adapted to operating within a confinement cell used in the nuclear industry. In particular, said conveyor is designed in such a way that the part ensuring the control thereof can be dissociated from the actual conveyor and placed outside the enclosure. This conveyor can also operate in an irradiated medium and its dimensions and cost permit its location in a cell and its periodic replacement.

The present invention therefore specifically relates to a stepwise advancing rotary conveyor, characterized in that it comprises a fixed base having a horizontal upper face onto which issues at least one injector communicating with pressurized gas supply means, a rotary plate resting by gravity on the upper face of the base and cooperating with said face by means for centering the plate about a fixed vertical axis, said plate having a circular outer edge, an upper face provided with receptacles distributed in ring-like manner about said axis and a lower face defining with the upper face of the base a central support chamber, at least one passage oriented in a direction inclined with respect to a radius passing through said axis being formed in the plate in order to connect the central support chamber and the outer edge of the plate in order to ensure a rotation of the latter when the supply means are actuated, the plate having a high weight such that the rotation is instantaneously stopped when the supply means are stopped, means for the remote detection of the presence of a receptacle in a given angular position about said axis and control means sensitive to signals supplied by the detection means in order to control the stoppage of the supply means when a receptacle is present in said angular position.

As such a conveyor operates without friction, it has no part which is subject to wear. In addition, it has a compact character and requires no invention. Moreover, the use of pressurized gases for rotating the plate ensures the automatic cleaning thereof. Finally, the absence of an electric current is a major advantage from the security standpoint, because all explosion risks are eliminated.

Obviously, although such a conveyor is particularly adapted for use within a confinement enclosure in the nuclear industry, it is readily apparent that it can also be used outside such an enclosure and for other applications.

In a particular embodiment of the invention, the remote detection means comprise an optical detector integral with the fixed base and reference marks formed on the rotary plate facing said detector in radial planes passing through each of the receptacles.

In order to ensure the initial positioning of the rotary plate, so that the passage of the bottles located in receptacles takes place in a given order, the conveyor can also comprise means for the remote marking of an initial angular position of the plate. These means e.g. comprise a second optical detector integral with the fixed base and a reference mark formed on the rotary plate facing said second detector in a radial plane passing through one of the receptacles.

In a particularly interesting improvement to the conveyor, the latter also comprises agitating means incorporating a second injector integral with the fixed base, pulsed pressurized gas supply means connected to said second injector and at least one pipe formed in the plate and having two ends respectively issuing into the bottom of one of the receptacles and into the face of the second injector in a given angular position of the plate.

As a result of these characteristics, it is possible to ensure the agitation or stirring of the bottles carried by the plate without having to use supplementary mechanisms. It is readily apparent that this improvement is particularly useful when such a conveyor is used for taking samples and then for diluting the samples taken.

The conveyor can also comprise an ejection station incorporating a third injector to which are connected pressurized gas supply means and a discharge chute or tube, whereof one end is placed above one of the receptacles for a given angular position of the plate, in which said pipe issues in front of the third injector.

The invention also relates to the application of such a conveyor to an installation for taking liquid samples from bottles sealed by caps.

According to the invention, the bottles containing the liquids from which samples are to be taken are placed in the receptacles of the plate of the conveyor and the installation is characterized in that it comprises, apart from the aforesaid conveyor, a fixed lateral gantry supporting a vertical sampling needle via means for displacing said needle vertically between an upper position authorizing the rotation of the plate and a lower sampling position, in which the cap is perforated by the needle, and a chromatographic valve equipped with a sampling loop, whereby said valve can occupy either a sampling position in which two first inlets, respectively communicating with the needle and with a suction venturi, are interconnected across said loop, or a sample discharge position, in which two other inlets of the valve, communicating respectively with means for ejecting a sample taken and with a sample discharge tube, are interconnected across said loop.

In such an installation, the sample ejection means preferably comprise means for simultaneously ejecting a known volume of liquid diluent. These means can in particular comprise a second chromatographic valve, whereof a first inlet communicates with a burette and is connected to a second inlet communicating with the first valve, in a first position of the second valve, said first inlet being connected to a third inlet communicating with a liquid diluent tank, in a second position of the second valve.

In this case, the receptacles are preferably spaced from one another by a given spacing on the plate and the bottles filled with liquid samples and the empty bottles are alternately placed in said receptacles. The lateral gantry then also supports a vertical reinjection needle displaced by the said spacing from the sampling needle, said reinjection needle being supported via second means for vertically displacing said needle between an upper position authorizing the rotation of the plate and a lower discharge position, in which the cap of an empty bottle is perforated by the reinjection needle, the latter communicating with the sample discharge tube.

In order that the diluted sample can in turn be sampled and supplied to an analyzer, the lateral gantry can also support a vertical needle for sampling the diluted sample and displaced by said spacing from the reinjection needle, said diluted sample taking needle being supported via third means for vertically displacing said needle between an upper position authorizing the rotation of the plate and a lower sampling position in which the cap of a bottle filled with the diluted sample is perforated by the needle for taking the diluted sample, said needle communicating with a sampling tube.

Preferably, said installation then also comprises a third chromatographic valve equipped with a second sampling loop, whereby said valve can occupy either a position of taking the diluted sample, in which two first inlets respectively communicating with the sampling tube and with a second suction venturi are interconnected across the second sampling loop, or a diluted sample discharge position, in which two other inlets of the third valve respectively communicating with a transfer liquid injection means and with an analysis means are interconnected across the second loop.

BRIEF DESCRIPTION OF THE DRAWING

A special embodiment of the invention will now be described in nonlimitative manner with reference to the attached drawings, wherein.

DESCRIPTION OF THE PREFERRED EMBODIMENT

Figure 1:
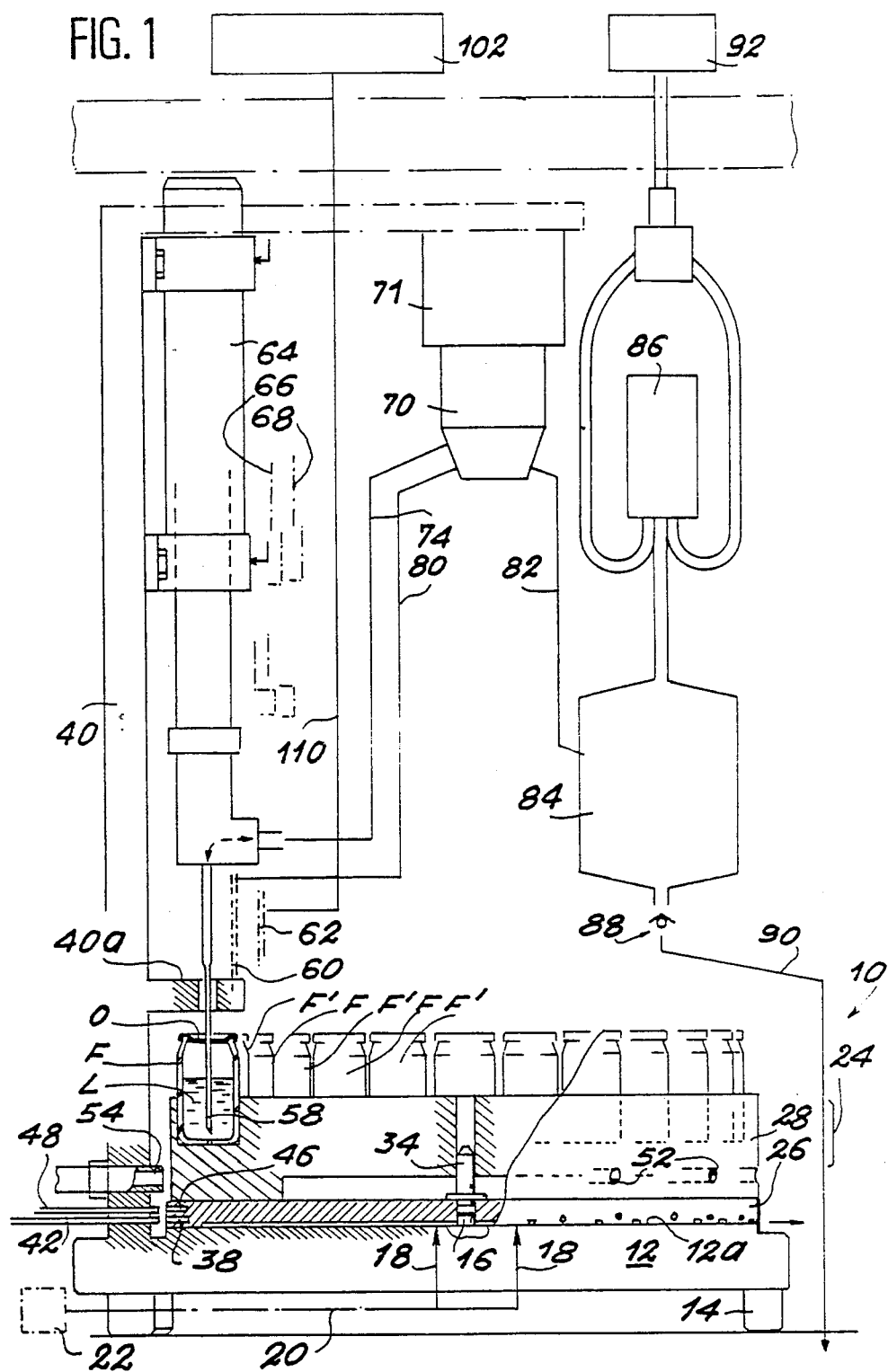
FIG. 1 is a side view diagrammatically showing in partial section an installation for taking liquid samples from bottles carried by a stepwise advancing rotary conveyor according to the invention.

The installation diagrammatically shown in FIG. 1 is designed to automatically take a sample of given volume from a radioactive liquid L contained in a bottle F sealed by a cap O, e.g. made from elastomer. When this sampling operation has been completed, the liquid sample and a certain volume of diluent are reinjected into a bottle F' identical to bottle F, but which is empty. The diluted sample is then agitated and then a given volume of said diluted sample is again removed from bottle F' and is then passed to a random type of analyzer.

Before describing in detail the installation making it possible to perform these various operations, it is pointed out that the invention is not limited to this particular application. Thus, the invention mainly relates to a rotary conveyor, no matter what the application thereof. Moreover, although the invention also relates to an installation for taking liquid samples, these samples can be of a random nature.

The stepwise advancing rotary conveyor designated by the general reference 10 in FIG. 1 comprises a fixed base 12, which can be placed on a random horizontal surface by means of feet 14. This fixed base 12 has an upper, planar, horizontal face 12a externally defined by a circular edge or rim.

As is shown in FIG. 1, a centering stud 16 vertically projects beyond the planar upper face 12a in accordance with the vertical axis thereof. For example three injectors 18 also issue onto the planar upper face 12a of base 12 in the vicinity of the centering stud 16. These injectors 18 communicate by a pipe 20 with a pressurized gas source 22 (FIG. 1). Fixed base 12 can in particular be made from plexiglass.

A rotary plate 24 rests by gravity on the upper face 12a of base 12. This plate 24 is constituted by a metal sheet 26 on which rests a solid part 28, e.g. made from plexiglass. The metal sheet 26, e.g. of stainless steel, is provided with a central bore 26a, in which is located the centering stud 16 carried by base 12 and constitutes the motor of conveyor 10. This sheet 26 has a high weight, e.g. approximately 4 kg for an external diameter of approximately 22 cm.

Sheet 26 rests on the planar upper face 12a of base 12 by a peripheral ring 26d (FIG. 3) projecting with respect to the remainder of its lower face 26b. In this way, the injectors 18 issue into a central chamber 30 (FIG. 2) defined between the planar upper face 12a of the base and the lower face 26b of the sheet.

Figure 3:
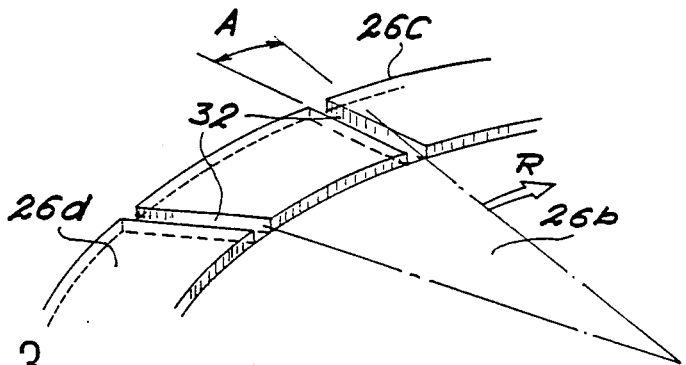
FIG. 3 is a perspective view showing part of the lower face of the rotary plate of the conveyor of FIG. 2.

As is shown in FIG. 3, grooves 32 are formed in ring 26d for linking the central chamber 30 with the cylindrical outer edge 26c of sheet 26.

These grooves are regularly distributed over the entire periphery of the ring and are all inclined in the same direction and by the same angle A with respect to radii passing through the vertical axis of plate 24.

As a result of the characteristics described hereinbefore, the arrival of the pressurized gas through the injectors 18 has two distinct effects on the plate 24.

Figure 2:
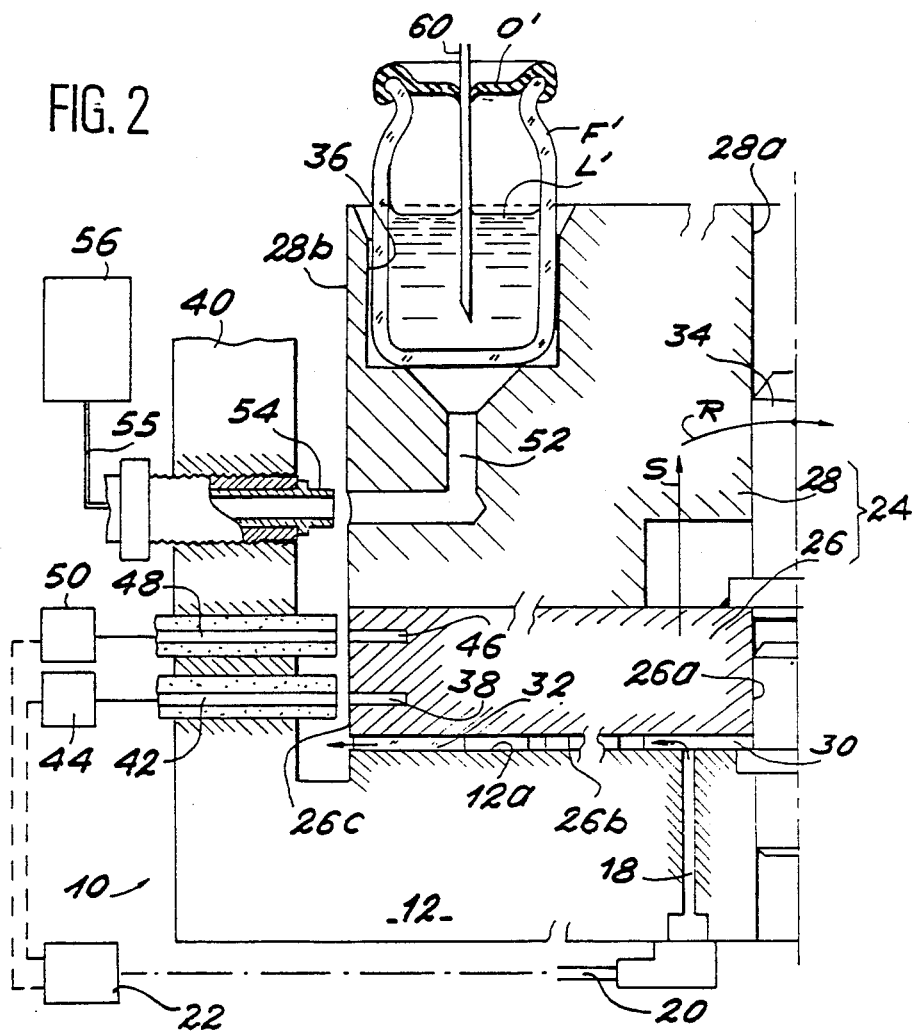
FIG. 2 is a sectional view of the conveyor used in the installation of FIG. 1 in accordance with a vertical plane passing through the rotation axis of the conveyor.

A first of these effects is to support the plate as a result of the pressurized gas entering the central chamber 30 (arrow S in FIG. 2). The second effect is to slowly rotate plate 24 as a result of the escape of compressed gas admitted into the central chamber 30 by grooves 32. Thus, the inclination of these grooves with respect to radii passing through the rotation axis of the plate creates a tangential component slowly rotating the plate in the direction of arrow R in FIGS. 2 and 3.

It is readily apparent that identical effects could be obtained by giving different shapes to the grooves 32, e.g. inwardly curved, or by replacing said grooves by passages traversing sheet 26 so as to link the central chamber 30 with the outer cylindrical edge 26c of said sheet.

According to an important feature of the invention, the weight of sheet 26 is sufficiently high for the rotation speed of plate 24 to remain low and for the rotation of the plate to be substantially instantaneously interrupted.

In the center of its upper planar face, sheet 26 carries a centering stud 34 which is located in a bore 28a formed in the center of part 28 of rotary plate 24. Part 28 rests by gravity only on sheet 26 so as to rotate with the latter. Part 28 supports the bottles F from which the liquid samples are to be taken, as well as the empty bottles F' into which the liquid samples are reinjected.

Part 28 has a cylindrical outer edge 28b of the same diameter as the cylindrical outer edge 26c of sheet 26. Receptacles 36 for bottles F and F' are formed by recesses provided in the outer portion of the upper face of part 28. These receptacles are regularly distributed in order to define between each of them a given angular spacing about the vertical rotation axis of plate 24. Receptacles 36 have identical shapes adapted to the shapes of the bottles F and F' which they are to receive. Moreover, they have vertical axes equidistant of the rotation axis of the plate. In the represented example, the receptacles 36 are cylindrical.

As a non-limitative example, plate 24 can be provided with twenty-four receptacles separated from one another by an angular spacing of 15°.

It should be noted that this conveyor can be adapted to other shapes of bottles or receptacles of different types by replacing the solid part 28 by a part having differently shaped recesses.

In order to reference mark the arrival of each of the receptacles 36 in a given angular position during the rotation of rotary plate 24, radially oriented blind holes 38 are made in the outer edge 26c of sheet 26 in the same horizontal plane, said holes 38 being angularly distributed with the same spacing as that separating receptacles 36. As a result of a not shown angular positioning finger formed on sheet 26 and which is located in a slot formed on the lower face of part 28, the latter is automatically positioned in such a way that each of the three blind holes 38 is located in a given radial plane, e.g. passing through the vertical axis of one of the receptacles 36.

As illustrated in FIGS. 1 and 2, a lateral gantry 40 integral with base 12 of conveyor 10 supports different members of the sample taking installation to be described hereinafter. In order to detect the arrival of one of the receptacles 36 of the rotary plate in front of one of the members carried by gantry 40, the latter supports the end of an optical fibre 42, which is radially oriented with respect to the vertical rotation axis of plate 24 and is located in the same horizontal plane as the blind holes 38. By placing at the other end of the optical fiber 42 a transceiver means 44 (FIG. 2), it is possible to instantaneously detect the arrival of a hole 38 in front of the end of the optical fiber 42 through the disappearance of the light signal normally reflected by the reflecting outer surface 26c of sheet 26.

It is apparent that the detection of the arrival of a blind hole 38 in front of the optical fiber 42 makes it possible to automatically control the stoppage of the injection of pressurized gas through injectors 18. Bearing in mind the characteristics described hereinbefore, the rotary plate 24 then instantaneously stops in the desired angular position and the corresponding operations can be carried out.

In order that said operations are carried out in a given order as from a predetermined bottle F, FIGS. 1 and 2 shows that single blind hole 46 radially oriented like the blind holes 38 and disposed in the same radial plane as one of them, but in different horizontal plane, can be formed on the outer edge 26c of sheet 26 to the right of the receptacle 36 containing the bottle F from which the first sample is to be taken.

The end of a second optical fiber 48 is then fixed to gantry 40, so as to be radially oriented and located in the same horizontal plane as blind hole 46. Like optical fiber 42, fiber 48 is connected by its other end to an optical transceiver means 50 transmitting an initialization signal when the blind hole 46 faces the end of optical fiber 48.

When such a process initialization device is provided, the signals emitted by detector 44 are not transmitted to the pressurized gas source 22 when an initialization signal has not been emitted by detector 50. Thus, plate 24 rotates until the blind hole 46 faces the end of the optical fiber 48. The stepwise advance of the rotary plate then takes place in the manner described hereinbefore.

Obviously, the assemblies constituted by holes 38 and optical fiber 42, as well as hole 46 and optical fiber 48 can be replaced by any device for the contact-free marking of the angular positions of plate 24. Moreover, the orientations of the holes and the corresponding ends of the fibres can be different from those described hereinbefore.

In the embodiment shown in the drawings, the conveyor 10 also comprises means for agitating or stirring the bottles F' when the diluted liquid sample L' (FIG. 2) has been introduced into these bottles.

As will be shown hereinafter, receptacles 36 alternately receive a bottle F containing a liquid from which a sample is to be taken and an initially empty bottle F'. The means for agitating the bottles only apply to the receptacles containing bottles F', every other receptacle being equipped with such means.

As illustrated in FIG. 2, these agitating means comprises a passage 52 connecting the bottom of each receptacle for receiving a bottle F' to the outer cylindrical edge 28b of part 28. More specifically, the end of the passage 52 issuing onto the outer face 28b is radially oriented with respect to said face, whereas the end of the passage 52 issuing into the bottom of receptacle 36 is oriented in accordance with the vertical axis of said receptacle.

In order to permit agitation or stirring, FIG. 2 shows that the gantry 40 also supports a radially oriented injector 54 disposed in a horizontal plane containing the ends of the passages 52 issuing onto the outer face 28b of part 28.

Injector 54 communicates by a tube 55 with a pulsed pressurized gas source 56 (pneumatic frequency generator). In this way, when injector 54 faces the end of one of the passages 52 and when source 56 is actuated, the bottle F' placed in the corresponding receptacle 36 performs a reciprocating movement in a vertical direction under the effect of the pulsed air injected by passage 52.

Preferably and as illustrated in FIG. 1, gantry 40 is equipped with a horizontal plate 40a, which is then vertically located above the bottle F' at a distance such that the latter cannot escape from its receptacle 36 during its stirring.

Part of the agitating means described hereinbefore can also be used for ejecting bottles F', when all the operations are finished. For this purpose, an ejection station is provided, which has another injector comparable to injector 54 and to which is connected a pressurized gas source. The arrival of pressurized gas through the passage 52 issuing beneath the bottle makes it possible to eject the latter, e.g. into a discharge tube or chute placed above the bottle.

The description of the liquid sample taking installation incorporating the stepwise advancing rotary conveyor 10 will now be described with more particular reference to FIGS. 1 and 4.

Figure 4:
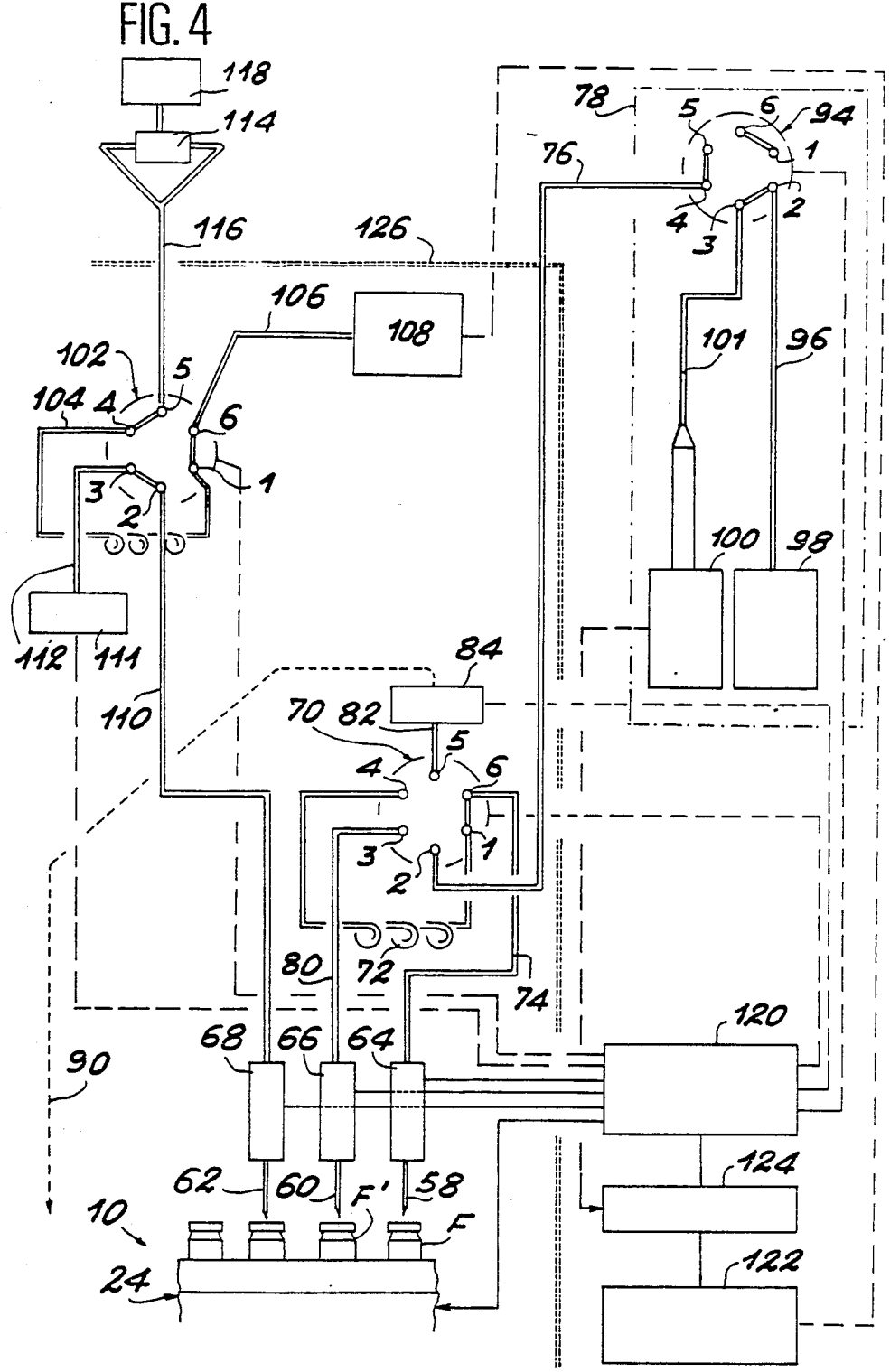
FIG. 4 diagrammatically shows the sample taking installation of FIG. 1 and in particular the pneumatic, hydraulic and electrical connections between the different components of said installation.

As can be seen in FIG. 1 and more diagrammatically in FIG. 4, the gantry 40 supports three vertical needles 58, 60, 62. These needles are arranged in such a way that they are all located above three successive bottles carried by plate 24, when a blind hole 38 faces optical fiber 42.

More specifically, needle 58 constitutes a sample taking needle, needle 60 a diluted sample reinjection needle and needle 62 a diluted sample taking needle. The rotation direction of the rotary plate 24 is such that each of the bottles F and F' successively passes in front of the needles 58, 60 and 62.

Each of the needles 58, 60, 62 is supported by gantry 40 via a double action jack 64, 66, 68 respectively. Each of these jacks makes it possible to vertically displace the corresponding needle between an upper position in which the needle is completely free from the bottle and permits the rotation of plate 24 and a lower position in which the corresponding needle passes through the cap O or O' sealing the bottle F or F' in order to be immersed in the latter.

Gantry 40 also supports a chromatographic valve 70, whereof the configuration can be more particularly gathered from FIG. 4. This valve 70 has six inlets 1 to 6 in FIG. 4. Inlets 1 and 4 are interconnected by a sampling loop 72, whose length determines the volume of sample to be taken. Inlet 6 of valve 70 communicates by a tube 74 with the sample taking needle 58. Inlet 2 communicates by a tube 76 with a liquid diluent injection device 78 and whose more detailed description will be given hereinafter. Inlet 3 of chromatographic valve 70 directly communicates with the diluted sample reinjection needle 60 by a tube 80. Finally, inlet 5 of valve 70 communicates by a tube 82 with a vacuum ampoule 84, which is also supported by the lateral gantry 40, as shown in FIG. 1.

Valve 70 is equipped with a pneumatic actuator 71 (FIG. 1) remotely controlled in the manner to be described hereinafter. All the tubes 72, 74, 76, 80 and 82 are made from stainless steel.

As illustrated in FIG. 1, the ampoule 84 communicates by its upper end with a venturi 86. Vacuum ampoule 84 is provided at its lower end with a non-return valve 88 making it possible to discharge the sampled liquid residues to a drainage system by a pipe 90. Venturi 86 is remotely controlled by a compressor 92.

In a first or sample taking position of valve 70 shown in FIG. 4, inlets 1 and 6 are interconnected, as are inlets 2 and 3 and inlets 4 and 5. The actuation of valve 70 makes it possible to pass it into a second position, where inlets 1 and 2, 3 and 4, 5 and 6 are interconnected. This second position is called the sample discharge position.

During the operation of conveyor 10, it has been seen that the rotation of plate 24 controlled by the injection of compressed air through injectors is automatically interrupted when a hole 38 arrives in front of the optical fiber 42. The plate is then immobilized in such a way that the needle 58 is located above a bottle F containing the liquid to be analyzed and needle 60 is located above an empty bottle F'.

Jack 64 is then automatically actuated so as to introduce the needle 58 into the corresponding bottle F. As the valve 70 is in the sample taking position shown in FIG. 4, the sample taking needle 58 is connected to venturi 86 via sampling loop 72.

The actuation of compressor 92 connected to venturi 86 then has the effect of sucking part of the liquid contained in bottle F into the vacuum ampoule 84, whereof the bottom is then sealed by the non-return valve 88. Thus, the sampling loop 72 is filled. Valve 70 is then switched over to bring it into its sample discharge position. Compressor 92 is then stopped, which has the effect of making the vacuum in ampoule 84 disappear. The liquid residue present in said ampoule is then automatically discharged by gravity to the drain due to the automatic opening of the non-return valve 88.

During the rotation of valve 70, a clearly defined liquid quantity is trapped in the sampling loop 72. Following the rotation of the valve, said liquid sample is placed between the dilution liquid injection device 78 and the diluted sample reinjection needle 60.

After perforating cap O' of bottle F' by actuating jack 66 controlling needle 60, the liquid sample trapped in the loop 72 is discharged, together with a certain quantity of dilution liquid within bottle F', which is initially empty, through using device 78.

In the embodiment shown in FIG. 4, this dilution liquid injection device 78 comprises another chromatographic valve 94, whose inlets are also numbered 1 to 6. Tube 76 is connected to inlet 4 of valve 94. Inlet 2 of said valve communicates by a tube 96 with a tank 98 containing the dilution liquid. Inlet 3 of valve 94 communicates with a dosing burette 100 by a tube 101. Finally, inlets 1, 5 and 6 are sealed by plugs. Valve 94 is rotated by a not shown pneumatic actuator.

In the position of valve 94 shown in FIG. 4, inlets 2 and 3 are interconnected, so that a given diluent volume can be sucked by burette 100 into tank 98. To this end, burette 100 is equipped with a stepwise motorization system. This sucking operation is carried out before the valve 70 passes into its sample discharge position. Valve 94 is then switched into a second position where inlets 3 and 4 are interconnected. In this position, the dilution liquid quantity contained in burette 100 and the liquid sample taken contained in loop 72 can be simultaneously delivered to bottle F' by needle 60 and is controlled by burette 100.

It is readily apparent that device 78 could be constructed differently. In particular, the chromatographic valve 94 could be replaced by a simple pneumatic three-way valve. The assembly formed by burette 100 and the valve can also be replaced by any equivalent system such as a dosing piston.

When the diluted sample has been discharged by needle 60 into bottle F' in the manner described hereinbefore, needles 58 and 60 are raised again.

A stirring or agitation of the sample is then generally necessary, so that its concentration within the diluent is as homogeneous as possible. It is at this instant that the agitating means of the bottle F' described hereinbefore with reference to FIG. 2 are put into operation. For this purpose, injector 54 is located in the radial plane passing through the axis of plate 24 and containing needle 60.

When agitation is ended, the diluted sample contained in bottle F', or at least part of said sample has to be taken and discharged into an analysis apparatus of a random type adapted to the measurements to be performed (e.g. spectrophotometric, spectrofluorimetric, radioactivity, pH, resistivity, turbidimetry or similar operations).

A rotation of rotary plate 24 is then controlled in order to bring the bottle F' into which has been introduced the diluted sample below needle 62. Jack 68 is then actuated in order to introduce the end of needle 62 into the solution contained in bottle F'.

In order to carry out the taking of the diluted sample contained in bottle F', when the latter arrives below needle 62, the installation also comprises in the embodiment shown in FIG. 4, another chromatographic valve 102, which can also be mounted on gantry 40. The six inlets of valve 102 are numbered 1 to 6 in FIG. 4.

In the represented embodiment, the chromatographic valve 102 is also equipped with a sampling loop 104 connecting inlets 1 and 4 and whose length makes it possible to determine the diluted sample volume supplied to an analyzer 108. Inlet 6 of valve 102 is connected by a tube 106 to analyzer 108. Inlet 2 is connected to the diluted sample taking needle 62 by a tube 110. A vacuum chamber 111 communicates with inlet 3 of valve 102 by a tube 112. Vacuum chamber 111 is identical to chamber 84 and communicates in the same way with a not shown venturi and draining system. Finally, inlet 5 of valve 102 is connected to a pump 114 by a tube 116.

Valve 102 is shown in FIG. 4 in its position of discharging the sample taken in loop 104 to analyzer 108. In this position, inlets 1 and 6, 2 and 3 and 4 and 5 of the valve are interconnected.

In a position for taking the diluted sample, inlets 1 and 2, 3 and 4 and 5 and 6 are interconnected. In this position, needle 62 is connected to vacuum chamber 111 via sampling loop 104. Taking the diluted sample in bottle F' then takes place in the same way as taking the undiluted sample controlled by the chromatographic valve 70. Thus, the actuation of the venturi associated with the vacuum chamber 111 has the effect of filling the sampling loop 104 with diluted sample.

In order to deliver the diluted sample trapped in loop 104 to analyzer 108, valve 102 is brought into the position shown in FIG. 4. Under these conditions, the sampling loop 104 is located between pump 114 and analyzer 108. The operation of pump 114 then has the effect of delivering the diluted sample in loop 104 to analyzer 108 by means of a transfer liquid taken from a tank 118.

The embodiment shown applies to the case where the analysis of the diluted sample involves taking a precise solution volume. As a variant, if the analysis does not require any volume accuracy, the solution can be directly sucked into the analyzer. In this case, analyzer 108 is placed between the diluted sample taking needle 62 and the vacuum chamber 111. Valve 102 and pump 114, together with the associated reservoir 118 are then eliminated. In this case a static measurement can be performed if necessary by stopping the venturi prior to the complete suction of the solution.

As is diagrammatically shown in FIG. 4, the installation also comprises an electrovalve box 120 for controlling all the pneumatic members of the installation. Box 120 controls jacks 64, 66 and 68 associated with each of the needles, as well as the linking of the compressed gas sources 22 and 56 respectively with injectors 18 and 54. Box 120 also controls the pneumatic actuators of the three chromatographic valves 70, 94 and 102, as well as the putting into operation of venturis 84 and 111.

Electrovalve box 120 is controlled by a programmable control logic 122 across an interface 124. Control logic 122 is sensitive to signals supplied by optical detectors 44 and 50, in order to control the electrovalve box 120 and the stepping motor of the burette 100 across interface 124 and in accordance with a predetermined program. Logic 122 can also be used for processing informations supplied by analyzer 108.

FIG. 4 also shows at 126 part of the wall of the confinement cell within which sampling takes place in the case of the nuclear industry. This illustration also clearly shows that apart from the rotary conveyor 10, needles 58, 60, 62, valves 70 and 102 and venturis 84 and 110, which are mounted on the lateral gantry 40, and the dosing means 108, all the other members of the installation are located outside the cell. This configuration makes it possible to limit the overall dimensions and costs of those parts of the installation located within the cell and simplifies maintenance. Moreover, all the members located within the cell are operated by compressed air, which makes it possible to avoid explosion risks and improves security.

Moreover, the quality and reproducibility of the sampling operations are improved by the use of chromatographic valves with sampling loops, whose precision is well known. The assembly controlled by the control logic 122 is also entirely automated once the bottles F and F' have been placed in their receptacles. The putting into place of the bottles on the plate does not form part of the invention. However, it is readily apparent that it can also be automated, if necessary.

Moreover, it has already been stated that the liquid sample taking installation according to the invention can undergo various modifications without passing beyond the scope of the invention. The installation can in particular be greatly simplified if there is not need to dilute the sample taken. In this case, gantry 40 supports a single sampling needle 58 and the valve 70 equipped with its venturi 84. Device 78 is then replaced by an assembly constituted by a pump and a transfer liquid tank comparable to pump 114 and tank 118. In this case, the outlet 3 of valve 70 is directly connected to analyzer 108.

It is possible to arrange in series a plurality of sampling chromatographic valves identical to valve 70, each of said valves being equipped with a sampling loop of different length. It is then possible to sample different volumes from individual bottles as a function of the nature of the analyses to be performed. Finally, the chromatographic valve or valves need not be supported by the gantry.

We claim:

1. An installation for taking liquid samples from bottles (F) sealed by caps (O), characterized in that said installation comprises a stepwise advancing rotary conveyor (10) comprising a fixed base (12) having a horizontal upper face (12a) onto which issues a first injector (18) communicating with pressurized gas supply means (22), a rotary plate (24) resting by gravity on the upper face of the base and cooperating with said face by means (16, 26a) for centering the plate about a fixed vertical axis. said plate having a circular outer edge (26c, 28b), an upper face provided with receptacles (36) distributed in ring-like manner about said axis and a lower face (26b) defining with the upper face (12a) of the base a central support chamber (30), at least one passage (32) oriented in a direction inclined with respect to a radius through said axis being formed in the plate (24) in order to connect the central support chamber and the outer edge of the plate in order to ensure rotation of the latter when the supply means (22) are actuated, the plate having a weight such that the rotation is instantaneously stopped when the supply means are stopped, remote detection means (38, 42, 44) operatively associated with said plate for the remote detection of the presence of one of said receptacles (36) in a given angular position about said axis, and control means (122, 120) operatively connected with said detection means sensitive to signals supplied by the detection means (44) in order to control the stoppage of the supply means (22) when said one of said receptacles (36) is present in said angular position, the bottles being placed in receptacles (36) of said plate, and whereby sad installation also incorporates a fixed lateral gantry (40) supporting a vertical sampling needle (58) via means (64) for displacing said needle vertically between an upper position authorizing the rotation of the plate and a lower sampling position, in which the cap is perforated by the needle, and a chromatographic valve (70) having a plurality of inlets and equipped with a sampling loop (72), whereby said valve can occupy either a sampling position in which two first inlets (6,5) of said plurality of inlets, respectively communicating with the needle (58) and with a suction venturi (86), are interconnected across said loop (72), or a sample discharge position, in which two other inlets (2,3) of said plurality of inlets of the valve, communicating respectively with means (78) for ejecting a sample taken and with a sample discharge tube (80), are interconnected across said loop (72).

2. An installation according to claim 1, characterized in that the sample ejection means incorporates means (78) for simultaneously ejecting a known liquid diluent volume.

3. An installation according to claim 2, characterized in that the means for ejecting a known liquid diluent volume incorporates a second chromatographic valve (94), whereof a first inlet (3) communicating with a burette (100) is connected to a second inlet (4) communicating with the first valve (70) in a first position of the second valve, said first inlet (3) being connected to a third inlet (2) communicating with a liquid diluent tank (98) in a second position of the second valve.

4. An installation according to claim 1, characterized in that with the receptacles (36) are spaced by a given spacing on plate, (24) the bottles (F) filled with liquid samples and with empty bottles (F') being alternately placed in the receptacles, the lateral gantry (40) also supports a vertical reinjection needle (60) displaced by said given spacing from the sampling needle (58), said reinjection needle being supported via second means (66) for vertically displacing said needle between an upper position authorizing the rotation of the plate and a lower discharge position in which a cap (O') of an empty bottle (F') is perforated by the reinjection needle (60), the latter communicating with the discharge tube of sample (80).

5. An installation according to claim 4, characterized in that the lateral gantry (40) also supports a vertical diluted sample taking needle (62) displaced by said spacing with respect to the reinjection needle (60), said diluted sample taking needle being supported via third means (68) for displacing said needle vertically between an upper position authorizing the rotation of the plate and a lower sampling position, in which a cap (O') of a bottle (F') filled with diluted sample is perforated by the diluted sample taking needle (62), the latter communicating with a sampling tube (110).

6. An installation according to claim 5, characterized in that it comprises a third chromatographic valve (102) having a plurality of inlets and provided with a second sampling loop (104), said third valve being able to occupy either a diluted sample taking position, in which two first inlets (2,3) of said plurality of inlets respectively communicating with the sampling tube (110) and with a second suction venturi are interconnected across the second sampling loop, or a diluted sample discharge position, in which two other inlets (5,6) of said plurality of inlets of the third valve, respectively communicating with a transfer liquid injection means (114) and an analyzer (108) are interconnected across the second loop (104).

7. A stepwise advancing rotary conveyor, characterized in that it comprises a fixed base (12) having a horizontal upper face (12a) onto which issues a first injector (18) communicating with pressurized gas supply means (22), a rotary plate (24) resting by gravity on the upper face of the base and cooperating with said face by means (16, 26a) for centering the plate about a fixed vertical axis, said plate having a circular outer edge (26c, 28b), an upper face provided with receptacles (36) distributed in ring-like manner about said axis and a lower face (26b) defining with the upper face (12a) of the base a central support chamber (30), at least one passage (32) oriented in a direction inclined with respect to a radius through said axis being formed in the plate (24) in order to connect the central support chamber and the outer edge of the plate in order to ensure rotation of the latter when the supply means (22) are actuated, the plate having a weight, such that the rotation is instantaneously stopped when the supply means are stopped, remote detection means (38, 42, 44) operatively associated with said plate for the remote detection of the presence of one of said receptacles (36) in a given angular position about said axis, and control means (122, 120) operatively connected with said detection means sensitive to signals supplied by the detection means (44) in order to control the stoppage of the supply means (22) when said one of said receptacles (36) is present in said angular position.

8. A stepwise conveyor according to claim 7, characterized in that the remote detection means comprise an optical detector (42) integral with the fixed base and reference marks (38) formed on the rotary plate (24) facing said detector in radial planes associated with each of the receptacles.

9. A stepwise conveyor according to claim 7, characterized in that said conveyor also comprises means for the remote marking of an initial angular position of the plate, comprising a second optical detector (48) integral with the fixed base and a reference mark (46) formed on the rotary plate (24) facing said second detector in a radial plane passing through one of the receptacles.

10. A stepwise conveyor according to claim 7, characterized in that said conveyor also comprises agitating means comprising a second injector (54) integral with the fixed base, pulsed pressurized gas supply means (56) connected to said second injector and at least one pipe (52) formed in the plate (24) and having two ends respectively issuing into the bottom of one of the receptacles (36) and in front of the second injector in a given angular position of the plate.

* * * * *